United States Patent
Shangguan et al.

(10) Patent No.: US 10,596,527 B2
(45) Date of Patent: Mar. 24, 2020

(54) AMORPHOUS FLUORINATED COPOLYMER GAS SEPARATION MEMBRANES

(71) Applicant: COMPACT MEMBRANE SYSTEMS, INC., Newport, DE (US)

(72) Inventors: Ning Shangguan, Cherry Hill, NJ (US); Andrew Edward Feiring, Wilmington, DE (US); Sudipto Majumdar, Newark, DE (US)

(73) Assignee: COMPACT MEMBRANE SYSTEMS, INC., Newport, DE (US)

( * ) Notice: Subject to any disclaimer, the term of this patent is extended or adjusted under 35 U.S.C. 154(b) by 78 days.

(21) Appl. No.: 15/574,408

(22) PCT Filed: Jun. 10, 2016

(86) PCT No.: PCT/US2016/036884
§ 371 (c)(1),
(2) Date: Nov. 15, 2017

(87) PCT Pub. No.: WO2016/201222
PCT Pub. Date: Dec. 15, 2016

(65) Prior Publication Data
US 2018/0133660 A1    May 17, 2018

Related U.S. Application Data

(60) Provisional application No. 62/174,936, filed on Jun. 12, 2015, provisional application No. 62/204,174, filed on Aug. 12, 2015.

(51) Int. Cl.
| | |
|---|---|
| *B01D 71/32* | (2006.01) |
| *B01D 53/22* | (2006.01) |
| *C08F 214/18* | (2006.01) |
| *C07C 17/38* | (2006.01) |
| *B01D 71/76* | (2006.01) |
| *B01D 67/00* | (2006.01) |
| *B01D 71/52* | (2006.01) |

(52) U.S. Cl.
CPC ........... *B01D 71/32* (2013.01); *B01D 53/228* (2013.01); *B01D 67/0006* (2013.01); *B01D 71/76* (2013.01); *C07C 17/38* (2013.01); *C08F 214/186* (2013.01); *B01D 71/52* (2013.01); *B01D 2323/06* (2013.01); *B01D 2323/08* (2013.01); *B01D 2325/20* (2013.01)

(58) Field of Classification Search
CPC ...... B01D 53/22; B01D 53/228; B01D 69/10; B01D 69/12; B01D 69/125; B01D 71/32; B01D 71/34; B01D 71/36; B01D 71/38; B01D 71/76; C08F 214/186

See application file for complete search history.

(56) References Cited

U.S. PATENT DOCUMENTS

| | | | |
|---|---|---|---|
| 3,758,603 | A | 9/1973 | Steigelmann et al. |
| 3,758,605 | A | 9/1973 | Hughes et al. |
| 4,557,955 | A * | 12/1985 | Walch .............. B01D 71/32 |
| | | | 204/296 |
| 4,614,524 | A | 9/1986 | Kraus |
| 4,731,263 | A | 3/1988 | Martin et al. |
| 5,015,268 | A | 5/1991 | Ho |
| 5,051,114 | A | 9/1991 | Nemser et al. |
| 5,062,866 | A | 11/1991 | Ho |
| 5,191,151 | A | 3/1993 | Eriksen et al. |
| 5,670,561 | A | 9/1997 | Pinnau et al. |
| 5,914,154 | A | 6/1999 | Nemser |
| 5,955,556 | A * | 9/1999 | McCarthy .......... C08F 214/186 |
| | | | 526/249 |
| 6,468,331 | B2 | 10/2002 | Kang et al. |
| 6,518,476 | B1 | 2/2003 | Culp et al. |
| 6,706,771 | B2 | 3/2004 | Kim et al. |
| 6,878,409 | B2 | 4/2005 | Kim et al. |
| 7,179,321 | B2 | 2/2007 | Kang et al. |
| 7,220,508 | B2 | 5/2007 | Watalabe et al. |
| 7,361,800 | B2 | 4/2008 | Hererra et al. |
| 7,491,262 | B2 | 2/2009 | Kang et al. |
| 2001/0025819 | A1 | 10/2001 | Bowser |
| 2003/0008990 | A1* | 1/2003 | McCarthy ............ C08F 214/04 |
| | | | 526/247 |

(Continued)

OTHER PUBLICATIONS

Maat et al., "The removal of hydrogen sulfide from gas streams using an aqueous metal sulfate A absorbent: Part 1. The absorption of hydrogen sulfide in metal sulfate solution" Separation and 1-11, 13-14 Purification Technology, vol. 43, No. 3, pp. 183-197 (2005) entire document, especially p. 183- 184.

*Primary Examiner* — Jason M Greene
(74) *Attorney, Agent, or Firm* — Devlin Law Firm LLC; James M. Lennon

(57) ABSTRACT

Membranes having a permselective active layer of a copolymerized perfluorinated monomer and an non-fluorinated alkylvinylester monomer demonstrate superior selective permeability performance for separating gas mixtures compared to membranes of exclusively perfluorinated polymers. Preferred active layer compositions are copolymers of perfluoro-2,2-dimethyl-1,3 dioxole (PDD) copolymerized with an alkylvinyl ester such as vinyl acetate, and vinyl pivalate, and with alkylvinyl esters that are substantially hydrolyzed to provide copolymerized vinyl alcohol functionality. The membranes can have a thin, high diffusion rate, "gutter layer" of a fluorinated polymer highly permeable to nitrogen positioned between the active layer and a porous support layer. A novel copolymer effective in selectively permeable membranes is a copolymer of PDD and an alkylvinyl ester compound having the formula $H_2C=CHOC(O)R^1$ in which $R^1$ is a linear or branched alkyl group of from 2 to 5 carbon atoms.

18 Claims, 1 Drawing Sheet

(56) References Cited

U.S. PATENT DOCUMENTS

| | | |
|---|---|---|
| 2003/0023015 A1 | 1/2003 | Tatemoto et al. |
| 2003/0033929 A1 | 2/2003 | Pinnau et al. |
| 2003/0104150 A1 | 6/2003 | Bonnet et al. |
| 2004/0050250 A1* | 3/2004 | Pinnau ................. B01D 53/228 95/45 |
| 2004/0102591 A1 | 5/2004 | Brookhart et al. |
| 2004/0167289 A1 | 8/2004 | Bekiarian et al. |
| 2005/0009944 A1 | 1/2005 | Apostolo et al. |
| 2007/0088142 A1 | 4/2007 | Ikeda et al. |
| 2011/0266220 A1* | 11/2011 | Campos ................. B01D 71/76 210/640 |
| 2012/0097612 A1 | 4/2012 | Nemser et al. |
| 2015/0025293 A1 | 1/2015 | Feiring et al. |
| 2015/0119577 A1 | 4/2015 | Campos et al. |
| 2017/0216780 A1* | 8/2017 | Kosar ................. B01D 71/34 |

* cited by examiner

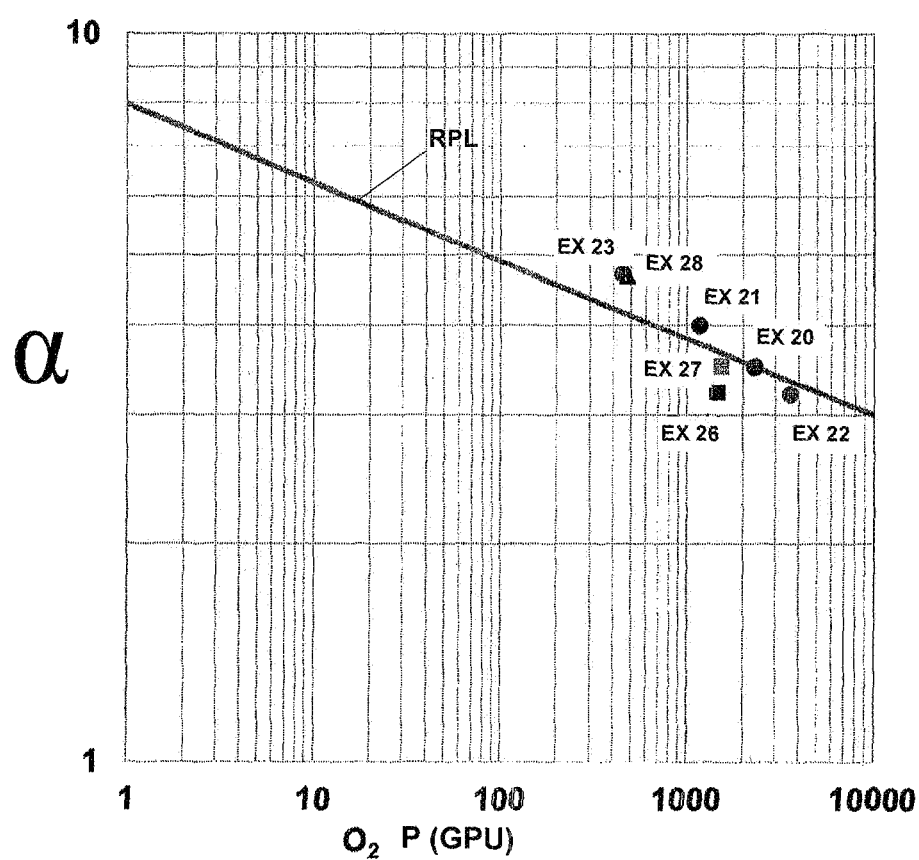

AMORPHOUS FLUORINATED COPOLYMER GAS SEPARATION MEMBRANES

This invention was made with government support under grant number DE-SC0011989 awarded by the Department of Energy. The government has certain rights in this invention.

FIELD OF THE INVENTION

This invention relates to the membrane separation of mixed gases such as oxygen and nitrogen mixtures. More particularly, it relates to such separations with membranes of fluorinated copolymer produced by copolymerization of comonomers comprising a perfluorinated cyclic or cyclizable compound and at least one from among (a) vinyl alcohol and (b) an alkylvinyl ester of structure $H_2C=CHOC(O)R$ in which R is a linear or branched alkyl group of from 1 to 5 carbon atoms.

BACKGROUND OF THE INVENTION

Using a membrane to separate components of fluid mixtures is well-developed technology of great commercial significance. Separations of commercial importance include oxygen/nitrogen, carbon dioxide/nitrogen, carbon dioxide/methane and water from alcohols. In general, membrane separation processes involve bringing a fluid mixture in contact with one side of a permeable membrane. The composition of the membrane is chosen so that the components of the mixture permeate through the membrane at different rates. The preferentially permeable component(s) permeate faster than the less permeable component(s) thereby effecting a separation of the components. The commercial utility of a gas separation membrane depends on both the rate at which the most permeable component passes through the membrane and on the relative rates of permeation of the given components of the mixtures, referred to as selectivity of the membrane.

It is clearly desirable to maximize both the permeation rate and selectivity so as to achieve the optimum separation of the components through a given membrane area and at given pressure. It is well recognized, however, that there tends to be a tradeoff between permeability and selectivity, that is, highly permeable membranes tend to have low selectivity and vice versa. This situation is described by the Robeson plot of selectivity vs. permeability of diverse gas mixtures that is well known in the field of membrane technology. In addition to permeability and selectivity, the ideal membrane should possess other desirable properties, such as high chemical stability to the components of the gas mixture, including minor components which may be present as contaminants. It should be thermally stable at its upper use temperature, be mechanically robust, and easy to fabricate into thin films.

Among the separations of substantial industrial interest is that of the components present in air. Air is a gas mixture comprising about 21 mol % oxygen, about 78 mol % nitrogen and small amounts of other components. The separation of air to provide oxygen enriched air (OEA) and/or nitrogen enriched air (NEA) is commercially significant. For example, NEA may be used to provide an inert gas composition in tanks carrying highly combustible liquid fuels. OEA may be fed to internal combustion engines to improve engine efficiency or used to treat patients having respiratory difficulties, for example.

U.S. Pat. No. 6,478,852 discloses nonporous polymeric membranes useful for producing nitrogen enriched air. Certain amorphous copolymers of perfluoro-2,2-dimethyl-1,3 dioxole (PDD) are particularily preferred because they have a unique combination of superior permeability and selectivity for a variety of gas mixtures. In some preferred embodiments, the copolymer is copolymerized PDD and at least one monomer of perfluorinated or partially fluorinated compounds selected from the group consisting of tetrafluoroethylene (TFE), perfluoromethylvinyl ether, vinylidene fluoride, hexafluoropropylene and chlorotrifluoroethylene. Copolymers of PDD and such comonomers are disclosed as nonporous gas permeable membranes in U.S. Pat. Nos. 5,914,154, 5,960,777 and 6,126,721.

U.S. Pat. No. 6,126,721 discloses a process to obtain oxygen enriched air using a membrane separation module. A particularly useful membrane structure employs a substrate of small diameter, microporous hollow fibers coated with a very thin layer of perfluoro-2,2-dimethyl-1,3 dioxole (PDD)/tetrafluoroethylene copolymer. In some preferred embodiments, the copolymer is copolymerized PDD and at least one monomer selected from the group consisting of tetrafluoroethylene, perfluoromethylvinyl ether, vinylidene fluoride and chlorotrifluoroethylene. In particular, the PDD/TFE copolymer is sold under the trademeark Teflon® AF (more fully described herein, below) and shows a highly desirable combination of properties as a membrane material, but even better membrane performance than that obtained from these PDD/TFE dipolymers is desirable.

U.S. Pat. Appl. No. 2005/0228152 discloses anti-reflective coatings comprising a fluorinated amorphous copolymer wherein said copolymer contains at least one functionalized repeating unit. Among the copolymers identified for this application is a copolymer of PDD and vinyl acetate.

U.S. Pat. No. 4,439,217 discloses polymers of vinyl pivalate as permselective elements for gas separations. The polymer may also contain olefinic compound comonomers. Among the olefinic comonomers cited are fluorinated olefins such as vinyl fluoride, vinylidene fluoride, tetrafluorotheylene, chlorotrifluoroethylene, and hexafluoropropylene. No cyclic or cyclizable perfluorinated comonomers are disclosed.

U.S. provisional application 62/174,936 discloses partially fluorinated polymeric membranes for separating mixed gases such as oxygen and nitrogen mixtures. Those membrane polymers are produced by copolymerization of monomers including a perfluorinated cyclic or cyclizable compound and an alkylvinyl ester of structure $H_2C=CHOC(O)R$ in which R is a linear or branched alkyl group of from 1 to 5 carbon atoms.

There is a continuing need for selectively permeable membranes that provide more effective separation of selected gas mixtures, such as oxygen and nitrogen in air, than are known in the art. It is especially desirable that the membrane have a sufficiently high glass transition temperature to allow separation operations at higher temperatures.

SUMMARY OF THE INVENTION

It now has been discovered that membranes of certain fluorinated copolymers demonstrate surprisingly superior selective permeability performance for separating gas mixtures such as $O_2/N_2$ mixtures. These are polymers of a copolymerized cyclic or cyclizable perfluorinated olefin monomer and an alkoxylated monomer. The preferred cyclic or cyclizable perfluorinated olefin monomer is perfluoro-2,2-dimethyl-1,3 dioxole (PDD). The alkoxylated monomer is an alkylvinyl ester, vinyl alcohol (VOH), or a mixture thereof. These membranes perform separations better than existing selectively permeable perfluorinated polymer membranes such as those of PDD/TFE copolymers.

The VOH-containing fluorinated copolymers are found to have a higher glass transition temperature typically greater than about 30° C. higher than copolymers of PDD and vinyl esters. Consequently, the novel membranes of perfluorinated olefin/VOH copolymers advantageously enable separation processing at higher temperatures. This invention also discloses membranes of previously unknown polymer compositions. Such novel copolymers comprise repeating units of copolymerized PDD and alkylvinyl ester compounds having the formula $H_2C=CHOC(O)R^1$ in which $R^1$ is a linear or branched alkyl group of from 2 to 5 carbon atoms.

Accordingly there is provided a membrane separation method comprising the steps of (i) providing a fluid mixture of feed components, (ii) providing a membrane comprising a gas selectively permeable, active layer including copolymerized monomers comprising (a) a perfluorinated cyclic or cyclizable olefin monomer and (b) an alkoxylated monomer, (iii) contacting a feed-retentate side of the membrane with the mixture, (iii) selectively permeating the mixture through the membrane to form a permeate composition on the permeate side of the membrane and a retentate composition in contact with the feed-retentate side of the membrane, and (iv) recovering from the membrane at least one of (a) the permeate composition enriched in faster permeating feed components relative to the mixture, and (b) the retentate composition depleted of faster permeating feed components relative to the mixture in which the alkoxylated monomer is selected from the group consisting of an alkylvinyl ester monomer having the formula $H_2C=CHOC(O)R$ in which R is a linear or branched alkyl group with 1 to 5 carbon atoms, a vinyl alcohol monomer, and a mixture of them.

There is also provided a selectively permeable separation membrane comprising an active layer comprising a copolymer of a perfluorinated cyclic or cyclizable olefin monomer and an alkoxylated monomer selected from the group consisting of an alkylvinyl ester monomer having the formula $H_2C=CHOC(O)R$ in which R is a linear or branched alkyl group with 1 to 5 carbon atoms, a vinyl alcohol monomer, and a mixture of them.

This invention further provides a polymer composition of copolymerized monomers comprising (a) a perfluorinated cyclic or cyclizable olefin monomer and (b) an alkylvinyl ester monomer having the formula $H_2C=CHOC(O)R^1$ in which $R^1$ is a linear or branched alkyl group of from 2 to 5 carbon atoms.

BRIEF DESCRIPTION OF THE DRAWINGS

FIG. 1 is a plot of oxygen/nitrogen selectivity vs. oxygen permeance exhibited by membranes according to embodiments of this invention in comparison to a modified Robeson Permeation Limit line in which the abscissa indicates permeability rather than permeance.

DETAILED DESCRIPTION OF THE INVENTION

The selectively permeable membranes suitable for this invention have an active layer of a fluorinated copolymer. This copolymer composition results from the copolymerization of monomers comprising a perfluorinated monomer and an alkoxylated monomer.

The perfluorinated monomer is a perfluorinated cyclic or cyclizable olefin monomer. Representative examples of the perfluorinated cyclic or cyclizable organic compound are perfluoro-2,2-dimethyl-1,3-dioxole ("PDD"), perfluoro-2-methylene-4-methyl-1,3-dioxolane ("PMD"), perfluoro (alkenyl vinylether) ("PFVE"), perfluoro(4-vinyloxyl-1-butene) (PVOB), and 2,2,4-trifluoro-5 trifluoromethoxy-1,3 dioxole ("TFMD"). PDD is preferred.

The fluorinated copolymer of the active layer composition may include fluorine substituted repeating units of copolymerized fluorine substituted monomers in addition to the perfluorinated cyclic or cyclizable olefin monomer. These added fluorine substituted monomers may or may not be cyclic or cyclizable olefins, and may be perfluorinated or partially fluorinated olefin compounds. Examples include acyclic fluorine substituted olefins. Representative suitable acyclic fluorinated olefins are tetrafluoroethylene (TFE), chlorotrifluoroethylene (CTFE), perfluoromethyl vinyl ether (PFMVE), vinyl fluoride (VF), vinylidene fluoride (VDF), trifluoroethylene and $CF_2=CFOR_f—X$ wherein $R_f$ is a straight chain or branched fluoroalkyl group having 2 to 10 carbon atoms optionally substituted by ether oxygens, and in which X is a group selected from $SO_2F$, $SO_3H$, $CO_2CH_3$, $CH_2OH$ and CN.

By alkylvinyl ester is meant a functionalized repeating unit derived by copolymerization of an organic compound having the formula $H_2C=CHOC(O)R$ in which R is a linear or branched alkyl group having from 1 to 5 carbon atoms. The alkoxylated monomer preferably is non-fluorinated. Preferable alkoxylated monomers are vinyl acetate ("VAc") in which R of unit B is $CH_3$, and vinyl pivalate ("VPI") in which R is $C(CH_3)_3$. When vinyl acetate is used as a comonomer, the acetate ester groups in the resulting polymer can be hydrolyzed to hydroxyl groups. Preferred copolymer compositions for the active layer according to this embodiment of the invention are PDD/VAc copolymer and PDD/VPI copolymer.

A mixture of alkoxylated monomers may be used such that the copolymer can comprise repeating units from a perfluorinated monomer and multiple different alkoxylated monomers. For example, polymerization of PDD with a mixture of VAc and VPI affords a terpolymer containing both acetate and pivalate ester repeating units.

Vinyl alcohol, i.e., $CH_2CH(OH)$, is well recognized in the art to to be unstable as such. Due to at most a fleeting existence as a monomer compound, direct copolymerization with the perfluorinated monomer is impracticable. Therefore, to form a perfluorinated monomer/VOH copolymer for the novel vinyl alcohol-containing copolymer membrane the perfluorinated monomer is copolymerized with an alkylvinyl ester of formula $H_2C=CHOC(O)R$ in which R is a linear or branched alkyl group having from 1 to 5 carbon atoms. Subsequently, the ester is hydrolyzed to a hydroxyl group. Hydrolysis is typically conducted in an alcohol or aqueous alcohol solution using a base such as ammonia or an alkali metal hydroxide to facilitate the reaction. Hydrolysis of the ester group might not proceed to completion in which instance the polymer of this invention can contain residual ester units. Preferably most of the alkylvinyl ester comonomer is converted to alcohol groups such that less than about 50% of repeating units B are alkylvinyl ester. More preferably less than about 10% of repeating units B are alkylvinyl ester such that at least about 90% of the ester units are converted. Thus in present context, vinyl alcohol monomer as occasionally used herein, means to refer to the fraction of alkylvinyl ester monomer that is hydrolyzed to contain a substituted hydroxyl group after the alkylvinyl ester monomer is copolymerized with the perfluorinated monomer. Accordingly, in a preferred embodiment, the active layer of the selectively permeable membrane comprises a copolymer of a perfluorinated monomer and an alkoxylated monomer in which copolymer at least about 50% of alkylvinyl ester repeating units are hydrolyzed.

The alkoxylated monomers can comprise two or more alkylvinyl ester compounds. When multiple vinyl ester monomers are used the alkylvinyl esters are converted to respective alcohols as described above. However, the rate of hydrolysis of the alkylvinyl ester groups present may differ causing selective hydrolysis of one type of ester in the partially fluorinated polymer as illustrated in the examples herein in which a PDD/VAc/VPI terpolymer is selectively converted to a PDD/VOH/VPI terpolymer. Alternatively, substantially all of the ester groups may be hydrolyzed under different conditions.

A membrane suitable for use according to this invention can be fabricated by providing the fluorinated copolymer typically as a solution in an effective solvent. The polymer can be synthesized in the solvent or dissolved in the solvent after synthesis. The concentration of solution can be adjusted by dilution with solvent to obtain optimim fluid viscosity for subsequent steps of fabrication. For many of the fluorinated copolymers of this invention common organic solvents such as acetone, lower alcohols, for example, ethanol and methanol the like, can be used.

For some of these polymers such as those having a large proportion of perfluorinated monomer repeating units, fluorosolvents may also be needed in mixture with organic solvents. By large proportion is meant at least about 20 mole percent of all comonomers. These fluorosolvents have been identified as being particularly effective for dissolving perfluoropolymers.

Representative fluorosolvents that are suitable for use include Fluorinert™ FC-75 and FC-770 Electronic Liquids, and Novec™ HFE-7100, Novec™ HFE-7200, and Novec™ 7300 Engineered Fluids also from 3M. Fluorinert FC-75 is a solvent of perfluorinated compounds primarily with 8 carbons, believed to include 2-butyltetrahydrofuran. Fluorinert FC770 contains C1-C3 perfluoro N-alkyl morpholines among other perfluorinated compounds. Novec HFE-7100 includes methyl nonafluoroisobutyl ether and methyl nonafluorobutyl ether. Novec HFE-7200 includes ethyl nonafluoroisobutyl ether and ethyl nonafluorobutyl ether. Novec 7300 contains 1,1,1,2,2,3,4,5,5,5-decafluoro-3-methoxy-4-(trifluoromethyl)-pentane. Another suitable fluorosolvent is Vertrel® XF specialty fluid which is 2,3-dihydroperfluoropentane available from DuPont Wilmington, Del.

A suitable production technique to fabricate a membrane uses the solution from which the solvent is removed to leave a solid membrane structure of the fluorinated copolymer. Preferably the active layer, i.e., the selectively permeable portion, of the membrane is non-porous. The active layer of fluorinated copolymer can be formed from solution to a self-supporting, monolithic film structure by depositing a layer of polymer solution on a releasable substrate, evaporating the solvent and stripping the membrane from the substrate. Usually the minimum thickness to provide structural integrity for a self-supporting, monolithic film of this polymer is so large that pressure gradient across the membrane is too large for most practical selective permeation processes.

In preferred embodiments, the membrane employed includes a composite structure comprising the active layer and a support layer of a structurally strong, substrate material. The support layer normally is not selectively permeable and typically the substrate material of the support layer is microporous. The substrate is coextensive with and can be in direct contact with the active layer. In the composite membrane, the active layer is made extremely thin to facilitate flow of the migrating mixture components during permeation. The support layer can be laminated on or otherwise affixed to the active layer. Preferably, and especially for hollow fiber membranes the active layer can be solution coated on a surface of the microporous substrate.

The substrate can be any microporous material that is chemically stable in presence of the feed composition. By "chemically stable" is meant that the substrate is able to maintain its structural integrity without significant deterioration after enduring contact with components of the feed composition. By "microporous" is meant that the structure has pores throughout and that form continuous interstices or passageways extending from one side of the substrate through the thickness to the other side such that the feed can pass through the substrate indiscriminately. Many conventional, readily available and thus generally inexpensive, microporous membrane substrate materials can be used. Representative examples of porous substrate material are polymers selected from the group consisting of polyacrylonitrile (PAN), polyether ether ketone (PEEK), polyvinylidene fluoride (PVDF), polytetrafluoroethylene (PTFE), polypropylene, polysulfone (PSF) and polyether sulfone (PES).

The composite membranes may include additional layers, such as a layer, sometimes known as a "gutter layer", between the microporous support material and the active, selective layer, or a protective layer on exposed surface of the active layer, i.e. on the side of the active layer opposite the microporous support. A gutter layer typically has multiple purposes. One is to coat the support with a material that seals small defects in the support surface. It also can provide a smooth, substantially completely defect-free surface onto which the selective layer may be coated. Another purpose is to provide a layer of material highly permeable to the compounds being separated so as to channel permeating molecules to the relatively widely spaced pores in the support layer. The protective layer shields the thin active layer from physical damage experienced in normal process operations.

In a much preferred embodiment, the composite membrane defines a structure including an active layer, gutter layer, and microporous support layer. Active and support layers are as described above. Occasionally in this disclosure, the terms "high diffusion rate layer" and "HDL" refer interchangeably to the gutter layer according to this invention. The HDL is positioned coextensively between the active and support layers such that the active layer is in direct contact with one side of the HDL and the support is in direct contact with the second side of the HDL opposite the active layer.

Although broadly described above, the precise mechanisms by which the HDL enhances overall selective permeation performance of the membrane are not fully understood. For example the HDL can help to improve adhesion between the active layer and the support layer. Thus the gutter layer composition should be chemically compatible with both the fluorine-containing active layer and the typically non-fluorinated support layer compositions and should possess good permeance and selectivity to the components of the feed mixture to be separated.

The HDL of this invention preferably comprises fluorinated polymers. In the fluorinated polymers in the HDL, preferably at least about 50%, more preferably at least about 70%, and very preferably at least about 90% are carbon fluorine groups. Especially preferably this polymer is a perfluorinated polymer, that is all the monomer being polymerized to repeat unit contain no hydrogen. Such perfluoropolymers may have very small amounts of "adventitious" carbon hydrogen groups from impure monomers, or groups such as initiator fragments bonded to chains.

Particularly preferred polymers for the HDL are copolymers of perfluoro(2,2-methyl-1,3-dioxole), (PDD) particularly if included in a perfluoropolymer. In any copolymer of the PDD it is preferred that at least about 50 mole percent of the total repeat units are derived from PDD, more preferably at least 80 mole percent. Generally, higher molar percentages of PDD are desired in all PDD copolymers, consistent with being able to process the polymers into a layer in the membrane. A preferred copolymer is that of PDD with tetrafluoroethylene, available as Teflon® AF (The Chemours Co., Wilmington, Del. 19899, USA) and for further information about Teflon® AF, see P. R. Resnick, et al., *Teflon AF Amorphous Fluoropolymers*, J. Schiers, Ed., *Modern Fluoropolymers*, John Wiley & Sons, New York, 1997, p. 397-420, which is hereby included by reference. A preferred grade of Teflon® AF is AF 2400, which is reported to contain 83 mole percent PDD, and 17 mole percent tetrafluoroethylene.

Other potentially useful polymer in the HDL include Cytop® fluoropolymer resin (reportedly a homopolymer of 1,1,2,4,4,5,5,6,7,7-decafluoro-3-oxa-1-,6-heptadiene) available from Asahi Glass, 1-5-1, Marunouchi, Chiyoda-ku, Tokyo 100-8405, Japan, and Hyflon® DA-type fluoropolymer resin, (reportedly a copolymer of tetrafluoroethylene and perfluoro(3-methoxy-1,3-dioxole) available from Solvay, SA, RUE DE RANSBEEK, 310, 1120 Bruxelles, Belgium.

Preferably the polymer(s) in of the HDL are so-called "glassy" polymers. By that is meant the polymer has no melting point above about 30° C. with a heat of fusion of 3 J/g or more when measured by Differential Scanning calorimetry using ASTM Test D3418-12e1 using a heating and cooling rate of 10° C./min, and measured on the second heat. Also a glassy polymer has a Glass Transition Temperature (Tg) above about 40° C., more preferably about 40° C. The Tg is measured according to ASTM Test D3418-12e1 at a heating and cooling rate of 10° C./min, and the Tg is taken as the midpoint (inflection point) of the transition on the second heat. Preferably the Tg is less than about 220° C., because, for instance, if the Tg is too high it may be difficult to dissolve the polymer to form a coating or layer.

The HDL should provide very low resistance to each component of the mixture to be separated and thereby allow high trans-layer flux of these components. The HDL should have a permanence to nitrogen of at least 250 GPU at about 25° C. Preferably this permanence should be at least about 500 GPU and more preferably at least about 1000 GPU, especially preferably about 1500 GPU, and very preferably at least about 2500 GPU, and most preferably at least about 5000 GPU. One can search for potential polymers useful for an HDL by finding the permeabilities to nitrogen of various otherwise suitable polymers, noting that permeability units are often presented as Barrers, which are $(1\times10^{-10})$ sec·cm/cm$^2$·s·cm Hg. One GPU equals 1 cm$^3$ at standard temperature and pressure per cm$^2$-s-cm Hg$\times10^6$). Although the HDL can be porous or nonporous, preferably it is nonporous.

To obtain high permeances for such layers these layer are typically made out of polymers which have a high permeability to the gas being tested, for example, nitrogen, and are generally quite thin, because the higher the thickness the lower the permeance. Preferably the HDL layer is about 0.05 µm to about 0.5 µm thick, more preferably about 0.05 µm to about 0.2 µm thick and very preferably \ about 0.05 µm to about 0.1 µm thick.

It may be difficult to measure permeances on layer by themselves that are so thin because of damage from forming and handling such thin layers. Thus the measurement of the permeance of the HDL can be measured with the HDL supported by a porous layer, the porous layer having a much higher permeance to the gas being tested than the HDL itself.

If the permanence to components of the mixture is high enough, a relatively thick layer of the HDL material may be used. In such case, a membrane having only two layers, i.e., the active layer supported by the HDL could be employed. However such nonporous very highly permeable materials are difficult to find and so typically a third layer (micro) porous support layer is added. As mentioned, this (micro) porous support layer contains many small pores through which the desired components may flow relatively unobstructed, allowing the HDL to be very thin so that the productivity of the composite membrane is high per unit area. This support layer may be made thick enough to physically support the entire three (or more) layer composite membrane without sacrificing much productivity.

Permeance of an HDL can be measured by the following procedure. A 47 mm diameter flat disc membrane of HDL material on a porous support is punched from a larger 3 inch diameter flat sheet membrane. The 47 mm disc is then placed in a stainless steel cross flow testing cell having a feed port, retentate port, a sweep inlet port, and a permeate port. Four hex bolts are used to tightly secure the membrane in the testing cell with a total active area of 13.85 cm$^2$.

The feed port of the cell is connected to a gas manifold consisting of 4 gases: nitrogen, oxygen, helium, and carbon dioxide. The retentate port is connected to a ball valve to dead end the gas flow as well as to purge the gas. One of the two permeate ports is shut and the other is connected to a flow meter. Nitrogen is brought up to pressure by a gas regulator and allowed to purge slowly for 1 minute. The retentate port is closed and a flow measurement can be taken from the permeate which is at atmospheric pressure. This process is repeated for three different feed pressures between 5 to 10 psig so that an average permeance can be calculated. The feed pressure, permeate flowrate, and temperature are recorded for the calculation. The permeance can be calculated by the equation: $Q=F/(A\cdot\Delta p)$ in which Q=gas permeance, F=permeate flow rate, $\Delta P$=transmembrane pressure difference, and A is the effective area of the membrane, in this instance 13.85 cm$^2$.

Other layers and layer configurations may be present in the composite membrane. For example in a contemplated embodiment, the multilayer composite membrane can further include a protective layer coextensively adjacent to the active layer on the side of the composite opposite the support layer. The structure of such composite can be described as protective layer/active layer/HDL/support layer, in which the "/" symbol indicates an interface between adjacent layers. The protective layer preferably is a composition of a high diffusion rate layer as described hereinabove. This second HDL protects the "exposed" surface of the active layer from contamination and perhaps degradation from materials in the mixture which is to be separated or other process materials that contact the composite membrane in the course of routine operations. Other useful layers and configurations will be apparent to those skilled in the art.

The membrane structure for use with this invention can be any of the well known configurations, such as flat sheet, hollow fiber, tubular, spiral wound and vortex devices (also known as "rotating" devices). Other useful configurations include pleated sheet and tube ribbon form. Hollow fiber composite membranes are much preferred.

The fluorinated copolymer membrane of this invention is used in a method for separation of fluid mixtures by selective permeation. The fluids at atmospheric pressure and temperature conditions are in the state of a gas, a liquid or a combination thereof. Primarily the present method is intended for separation of gas mixtures. A mixture to be separated is placed in contact with one side (i.e., the "feed-retentate side") of the membrane. Conditions on both sides of the membrane, such as temperature, pressure, and partial pressure of the components, are maintained to impose a driving force for the permeation of the components of the feed mixture. The mixture components permeate through the membrane to the opposite, (i.e., "permeate") side of the membrane. The transmembrane migration speeds of individual components differ from each other depending on the permeability property of the individual components and driving force for the individual components, that is, for example, the transmembrane partial pressure difference. In comparison to the composition of the mixture fed to the membrane, a composition enriched in the faster migrating component(s) forms on the permeate side and a composition depleted of the faster migrating component(s) and thus enriched in the slower migrating component(s) forms on the feed-retentate side. The enriched compositions can be recovered for utilitarian purposes.

The membrane of fluorinated copolymer and the method of this invention are useful for separating the components of many chemical mixtures that have substantial industrial importance. Representative gases for which selective permeation through the novel membrane of this invention is considered suitable include the pure components and inorganic compounds oxgen, nitrogen, hydrogen, helium, carbon dioxide, and water vapor. For example, the method can be used to separate such mixtures of these as oxygen/nitrogen, and carbon dioxide/nitrogen. Separation of inorganics from hydrocarbons such as a carbon dioxide/methane blend is contemplated, however separations of hydrocarbons using membranes according to this invention such as separating alkanes or alkenes from alkane/alkene mixtures is not preferred.

This method is deemed especially valuable for producing highly concentrated nitrogen and oxygen products for various commercial uses. The method can be used to separate ordinary air into nitrogen enriched air ("NEA") and/or oxygen enriched air ("OEA"). The combination of oxygen/nitrogen selectivity and oxygen permeance afforded by the present invention is remarkable. The oxygen/nitrogen separation performance is consistently at and sometimes determined to exceed the previously understood theoretical limits.

EXAMPLES

This invention is now illustrated by examples of certain representative embodiments thereof, wherein all parts, proportions and percentages are by weight unless otherwise indicated. The entire disclosures of U.S. patents and patent applications identified in this application are hereby incorporated by reference herein.

Example 1. Synthesis of 100:250 Feed Mole Ratio PDD/VAc Copolymer

A round bottom glass pressure vessel equipped with a magnetic stirrer was immersed into an ice bath, flushed with argon and then loaded with 10 mL of Vertrel® XF (2,3-dihydrodecafluoropentane), 3.52 g vinyl acetate, 4.0 g PDD and 0.4 mL HFPO dimer peroxide (0.12 M). HFPO dimer peroxide was made from reaction of $CF_3CF_2CF_2OCF(CF_3)$ CFO with sodium percarbonate. The vessel was sealed and the reaction mixture was warmed to room temperature by immersing in a water bath. The reaction mixture was stirred overnight at room temperature. The vessel was opened to air and 30 mL methanol was poured in while stirring. The resulting solution was dried at room temperature for 1 hour and then in an oven at 100° C. for 3 hours. The resulting solids were further dried in a vacuum oven at 100° C. for 3 hours to get 4.3 g nearly white chunks of PDD/VAc copolymer product having a glass transition temperature, Tg, of 71° C. and intrinsic viscosity of 0.716 dL/g measured in 1-butanone solution at 25° C.

Example 2. Hydrolysis of PDD/VAc Copolymer of Example 1 to PDD/VOH Copolymer A round bottom glass flask equipped with a magnetic stirrer was loaded with 2.3 g of PDD/VAc copolymer prepared in Ex. 1, 50 mL methanol and 10.0 mL of 7.0 M ammonia solution in methanol. After the mixture was stirred for 2 days at room temperature, 80 mL of water was poured in while stirring. The resulting mixture was heated to 90° C. to evaporate methanol. After cooling to room temperature, the remaining water was decanted leaving brown solid that was then washed twice with 30 mL water. The solid was collected and dried in an oven at 100° C. overnight. The resulting product was 1.75 g of brown solid PDD/VOH copolymer having Tg of 132° C. and intrinsic viscosity of 0.884 dL/g measured in methanol solution at 25° C. The Tg value was substantially higher than its PDD/VAc precursor of Ex 1.

Example 3. Membrane Formation and Testing of Example 2 PDD/VOH Copolymer

PDD/VOH copolymer of Ex. 2 was dissolved in methanol to make a 0.07% solution. Teflon® AF 2400 was dissolved in Electronic Liquid FC770 (3M Company, Minneapolis, Minn.) to make a 0.15% solution. The 0.15% Teflon AF solution was coated on a PAN 350 (SEPRO Membranes Inc., Oceanside, Calif.) polyacrylonitrile, porous, flat sheet, asymmetric ultrafiltration membranehaving a molecular weight cut off rating of 150 Kdaltons. Coating was accomplished by covering the small pore side of the PAN 350 membrane with the liquid solution then standing the sheet on edge to drain excess solution vertically from the surface by gravity in an atmosphere less than 30% relative humidity (RH). After draining, the coating was dried of the Electronic Liquid FC770 at room temperature for 10 minutes then in a 65° C. oven for 15 minutes to form an HDL. Coating i preferred at humidity less than 30% RH to prevent water condensation on the coating surface which can adversely interfere with formation of a continuous HDL. The PDD/VOH solution was coated on the Teflon AF 2400 gutter layer then the methanol was removed to create the active layer. A second coating of the Teflon AF 2400 solution was placed on the exposed side of the PDD/VOH polymer layer after which Electronic Liquid FC-770 was removed to form a protective layer on the active layer.

The composite membrane was die cut to a 47 mm diameter disk that was placed in a flat, circular permeation test cell with an effective permeation area of 13.85 cm$^2$ and the permeances in GPU of oxygen, nitrogen, helium and carbon dioxide gases through the membrane were separately determined at room temperature (approximately 27° C.). A GPU is defined as 1 cm$^3$/cm$^2$-sec-cm Hg×10$^{-6}$ (STP). Results are presented in Table 1.

TABLE 1

Single gas tests

|  | N$_2$ | O$_2$ | He | CO$_2$ |
|---|---|---|---|---|
| Permeance (GPU) | 25.6 | 132 | 3,075 | 423 |

The same composite membrane in the permeation test cell was also used to determine O$_2$ and N$_2$ permeance and selectivity with mixed gas (air) at room temperature and 75° C. For these determinations, the stage cut, i.e., ratio of permeate flow rate to feed flow rate, was less than 1%. This made the oxygen concentration in the retentate to be almost the same as that in the feed for precise and easy analytical calculation. For testing at 75° C., the membrane cell and a long feed tube were put in a heated oven. The membrane feed pressure was at 15-75 psig (103-520 kPa) and the permeate pressure was atmospheric, i.e., 14.7 psia (101 kPa). Results of the mixed gas tests are shown in Table 2.

Selectivity, α, in the mixed gas operations was calculated using formula (I)

$$\alpha = (F_1 \times \Delta P_1)/(F_2 \times \Delta P_2) \quad (I)$$

in which $F_1$ is O$_2$ transmembrane flow, $F_2$ is N$_2$ transmembrane flow $\Delta P_1$ is partial pressure gradiant across the membrane of O$_2$, and $\Delta P_2$ is partial pressure gradiant across the membrane of N$_2$.

TABLE 2

Mixed gas tests

| Permeation Temperature | Room Temp. | 75° C. |
|---|---|---|
| N$_2$ Permeance (GPU) | 25.2 | 102 |
| O$_2$ Permeance (GPU) | 126 | 359 |
| O$_2$/N$_2$ Selectivity | 5.00 | 3.53 |

Example 4. Synthesis of 100:100 Feed Mole Ratio PDD/VAc Copolymer

A round bottom glass pressure vessel equipped with a magnetic stirrer was immersed into an ice bath, flushed with argon and then loaded with 15 mL of Vertrel XF, 3.44 g vinyl acetate, 9.76 g PDD and 0.8 mL HFPO dimer peroxide (0.12 M). The vessel was sealed and the reaction mixture was warmed to room temperature by immersing into a water bath. The reaction mixture was stirred overnight at room temperature. The vessel was opened to air and 60 mL methanol was poured in while stirring. The resulting sticky solids were filtered, washed with 20 mL methanol and dried in an oven at 100° C. for 3 hours. The solids were further dried in a vacuum oven at 100° C. overnight to get 8.7 g white chunks of PDD/VAc copolymer product having a Tg of 87° C.

Example 5. Hydrolysis of PDD/VAc Copolymer of Example 4 to PDD/VOH Copolymer

A round bottom glass flask equipped with a magnetic stirrer was loaded with 1.2 g of the PDD/VAc copolymer from Ex. 4, 40 mL methanol and 5.0 mL of 7.0 M ammonia solution in methanol. The mixture was stirred for 4 days at room temperature. and then 50 mL water was poured in while stirring. The resulting mixture was heated to 90° C. to evaporate the methanol. After cooling to room temperature, 20 mL of 10% MgSO$_4$ solution was added and the resulting precipitate was separated by centrifuge. The solid was collected and dried in an oven at 100° C. overnight. A nearly white solid (0.94 g) PDD/VOH product having Tg of 141° C. was obtained.

Example 6. Membrane Formation and Testing of Example 5 PDD/VOH Copolymer

The procedure of Ex. 3 was repeated using the PDD/VOH polymer of Ex. 5 as the active layer composition except that the PDD/VOH solution was 0.09% in methanol. Permeance data of single gases through the composite membrane is reported in Table 3.

TABLE 3

|  | N2 | O2 | He | CO$_2$ |
|---|---|---|---|---|
| Permeance (GPU) | 261 | 988 | 7162 | 3122 |

Example 7. Synthesis of 100:150 Feed Mole Ratio PDD/VAc Copolymer

A round bottom glass pressure vessel equipped with a magnetic stirrer was immersed into an ice bath, flushed with argon and then loaded with 8 mL of Vertrel XF, 2.12 g vinyl acetate, 4.0 g PDD and 0.4 mL HFPO dimer peroxide (0.12 M). The vessel was sealed and the reaction mixture was warmed to room temperature by immersing into a water bath. The reaction mixture was stirred overnight at room temperature. The vessel was opened to air and 60 mL methanol was poured in while stirring. The resulting precipitates were filtered, washed with 20 mL methanol and dried in an oven at 100° C. for 3 hours. The solids were further dried in a vacuum oven at 100° C. for 3 hours to get 3.8 g white chunks of PDD/VAc product copolymer having Tg of 79° C.

Example 8. Hydrolysis of PDD/VAc Copolymer of Example 7 to PDD/VOH Copolymer

A round bottom glass flask equipped with a magnetic stirrer was loaded with 0.8 g of PDD/VAc copolymer of Ex. 7, 40 mL methanol and 5.0 mL of 7.0 M ammonia solution in methanol. The mixture was stirred for 4 days at room temperature then 50 mL water was poured in while stirring. The resulting mixture was heated to 90° C. to evaporate the methanol. After cooling to room temperature, 20 mL of 10% MgSO$_4$ solution was added and the resulting precipitate was separated by centrifuge. The solid was collected and dried in an oven at 100° C. overnight. A nearly white solid (0.64 g) of PDD/VOH product copolymer having a Tg of 138° C. was obtained.

Example 9. Membrane Formation and Testing of Example 8 PDD/VOH Copolymer

The procedure of Ex. 3 was repeated except that the PDD/VOH copolymer of Ex. 8 was used to create the active layer of the membrane. Selected single gas permeance and mixed gas $O_2/N_2$ permeance and selectivity were determined and analytical results are shown in Tables 4 and 5, respectively.

TABLE 4

|  | $N_2$ | $O_2$ | He | $CO_2$ |
|---|---|---|---|---|
| Permeance (GPU) | 46.5 | 218 | 3,918 | 714 |

TABLE 5

| Permeation Temperature | Room Temp. | 75° C. |
|---|---|---|
| $N_2$ Permeance (GPU) | 57 | 151 |
| $O_2$ Permeance (GPU) | 246 | 465 |
| $O_2/N_2$ Selectivity | 4.31 | 3.09 |

Example 10. Synthesis of 100:250:50 Feed Mole Ratio PDD/VAc/VPI Terpolymer

A round bottom glass pressure vessel equipped with a magnetic stirrer was immersed into an ice bath, flushed with argon and then loaded with 10 mL of Vertrel XF, 3.52 g vinyl acetate, 1.05 g vinyl pivalate, 4.0 g PDD and 0.4 mL HFPO dimer peroxide (0.12 M). The vessel was sealed and the reaction mixture was warmed to room temperature by immersing in a water bath. The reaction mixture was stirred overnight at room temperature. The vessel was opened to air and 30 mL methanol was poured in while stirring. The resulting solution was dried at room temperature for 1 hour and then in an atmospheric pressure oven at 100° C. for 3 hours. The resulting solids were further dried in a vacuum oven at 100° C. for 3 hours to get 4.2 g pale brownish chunks of PDD/VAc/VPI terpolymer product having Tg of 70° C.

Example 11. Selective Hydrolysis of the Polymer of Example 10 to PDD/VOH/VPI Polymer A round bottom glass flask equipped with a magnetic stirrer was loaded with 1.6 g of the PDD/VAc/VPI terpolymer of Ex. 10, 20 mL methanol and 7.0 mL of 7.0M ammonia solution in methanol. The mixture was stirred for 2 days at room temperature then 30 mL water was poured in while stirring. The resulting mixture was heated to 90° C. to evaporate the methanol. After cooling to room temperature, 30 mL water was added followed by addition of 20 mL of 10% MgSO4 aqueous solution. The resulting precipitate was collected and dried in an oven at 100° C. overnight. Because a relatively weak base was used to hydrolyze the fluorinated olefin/alkylvinyl ester terpolymer, mainly the vinyl acetate and substantially none of the vinyl pivalate repeating units hydrolyzed to alcohol. Brownish solid (1.39 g) of PDD/VOH/VPI terpolymer product having Tg of 111° C.

Example 12. Membrane Formation and Testing of Example 11 PDD/VOH/PVI Polymer

The procedure of Ex. 3 was repeated except that the PDD/VOH/VPI terpolymer of Ex. 11 was dissolved in methanol to make a 0.1% solution used to create the active layer of the membrane. Selected single gas permeance (Table 6) and mixed gas $O_2/N_2$ permeance and selectivity (Table 7) were determined and analytical results are shown below.

TABLE 6

|  | $N_2$ | $O_2$ | He | $CO_2$ |
|---|---|---|---|---|
| Permeance (GPU) | 64.3 | 280 | 3,064 | 931 |

TABLE 7

| Permeation Temperature | Room Temp. | 75° C. |
|---|---|---|
| $N_2$ Permeance (GPU) | 56.6 | 169 |
| $O_2$ Permeance (GPU) | 256 | 549 |
| $O_2/N_2$ Selectivity | 4.53 | 3.25 |

Example 13. More Complete Hydrolysis of PDD/VAc/PVI to PDD/VOH Polymer

In this example, the PDD/VAc/PVI fluorinated olefin/alkylvinyl ester terpolymer was hydrolyzed with a stronger base compared to Ex. 11. This caused the vinyl pivalate repeating units as well as the vinyl acetate repeating units to hydrolyze to alcohol. A round bottom glass flask equipped with a magnetic stirrer was loaded with 0.6 g of PDD/VAc/VPI terpolymer of Ex. 10, 20 mL methanol, and 3 mL 5% KOH aqueous solution. The mixture was stirred for 2 days at room temperature, then 30 mL water was poured in while stirring. The resulting precipitate was collected and dried in an oven at 100° C. overnight. Brownish solid (0.33 g) was obtained of PDD/vinyl alcohol polymer product with a Tg of 130° C.). The higher Tg of this product is consistent with more complete hydrolysis of the ester groups relative to the partially hydrolyzed product of Ex. 11.

Example 14. Synthesis of 100:150 Feed Mole Ratio PDD/VAc Copolymer

A round bottom glass pressure vessel equipped with a magnetic stirrer was immersed into an ice bath, flushed with argon and then loaded with 15 mL of Vertrel XF, 2.58 g vinyl acetate, 4.88 g PDD and 0.5 mL HFPO dimer peroxide (0.12 M). The vessel was sealed and the reaction mixture was warmed to room temperature by immersing in a water bath. The reaction mixture was stirred overnight at room temperature. The vessel was opened to air and 30 mL acetone was poured in while stirring. The resulting mixture was dried at room temperature for 1 hour and then in an oven at 100° C. for 3 hours. The resulting solids were further dried in a vacuum oven at 100° C. for 3 hours to get 4.8 g slight yellowish chunks of PDD/VAc copolymer product having a glass transition temperature, Tg, of 78° C.

Example 15. Hydrolysis of PDD/VAc Copolymer of Example 14 to PDD/VOH Copolymer

A round bottom glass flask equipped with a magnetic stirrer was loaded with 4.2 g of PDD/VAc copolymer prepared in Ex. 14, 50 mL methanol and 20.0 mL of 7.0 M ammonia solution in methanol. After the mixture was stirred for 3 days at room temperature, 120 mL of water was poured in while stirring. The resulting mixture was heated to 90° C. to evaporate methanol. After cooling to room temperature, the remaining water was decanted leaving a brown solid that was then washed twice with 50 mL water. The solid was collected and dried in an oven at 100° C. overnight. The resulting product was 2.5 g of brown solid PDD/VOH copolymer having Tg of 138° C. This Tg value was substantially higher than its PDD/VAc precursor of Ex 14.

Example 16. Fabrication of a Tri-Layer Hollow Fiber Membrane with Active Layer of PDD/VOH Copolymer PDD/VOH copolymer of Ex. 15 was dissolved in methanol to make a 0.6% solution. Teflon® AF 2400 was dissolved in Electronic Liquid FC770 (3M Company, Minneapolis, Minn.) to make a 0.3% solution. The 0.3% Teflon AF solution was coated on the external surface of 0.457 mm outer diameter, PES porous hollow fibers Creating an HDL was accomplished by dipping and holding the fibers vertically in the solution for 10 seconds then withdrawing the fibers from the solution at about 1 m/min. The fibers were dried at room temperature at less than 30% RH for 10 minutes then were suspended in a 70° C. oven for 15 minutes to complete removal of the Electronic Liquid FC770. The PDD/VOH solution was similarly coated on the Teflon AF 2400 HDL then the methanol was removed to create a dry active layer adjacent the HDL. A second layer of the Teflon AF 2400 solution was coated on the exposed side of the PDD/VOH polymer layer after which Electronic Liquid FC-770 was removed to form a protective layer on the active layer. HDL, active layer and protective layer were each estimated to be about 0.3 μm thick.

Five composite hollow fibers prepared as above were assembled in a mini-permeation test module. Active fiber length in the module was 18.5 cm. The fiber bundle was potted at each end with an epoxy resin to provide 18.5 cm active fiber length and 13.26 $cm^2$ total active permeation area. Oxygen and nitrogen permeance in GPU of oxygen and nitrogen gases through the hollow fiber membrane module was separately determined at room temperature (R.T., approximately 23° C.) and 60° C. The feed gas is permeated through hollow fiber lumen side to the shell side. Results are presented in Table 8.

TABLE 8

|  | R.T. | 60° C. |
|---|---|---|
| $N_2$ Permeance (GPU) | 100 | 163 |
| $O_2$ Permeance (GPU) | 379 | 538 |
| $O_2/N_2$ Selectivity | 3.79 | 3.30 |

Compressed air (20.9 vol. % $O_2$) at 45 psig was fed to the mini-permeation test module from the hollow fiber lumen side. Nitrogen enriched air of greater than 95 vol. % $N_2$ was obtained as a retentate stream at a 69.2% stage cut at room temperature. In a separate trial a 76.2% stage cut was obtained at 60° C. The pressure of permeate oxygen enriched air was 0 psig. Data from these permeation trials are presented in Table 9.

TABLE 9

| Trial | 1 | 2 |
|---|---|---|
| Temperature (° C.) | 24.5 | 60 |
| Feed Pressure (psig) | 44.8 | 45.1 |
| Permeate Flow (mL/min.) | 27.9 | 51.9 |
| Permeate $O_2$ (vol. %) | 28.1 | 25.8 |
| Retentate Flow (mL/min.) | 12.4 | 16.2 |
| Retentate $O_2$ (vol. %) | 4.9 | 4.9 |
| Stage Cut (%) | 69.2 | 76.2 |

Example 17. Synthesis of 100:200 PDD/VAc Monomer Mole Ratio Copolymer

A round bottom glass pressure vessel equipped with a magnetic stirrer was immersed in an ice bath, flushed with argon and then loaded with 10 mL of Vertrel XF fluid, 2.82 g vinyl acetate, 4.0 g PDD and 0.4 mL HFPO dimer peroxide (0.12 M). The vessel was sealed and the reaction mixture was warmed to room temperature by immersing into a water bath. The reaction mixture was stirred overnight at room temperature. The vessel was opened to air and 20 mL acetone was poured in with stirring. The resulting solution was dried at room temperature for 1 hour and then in an oven at 100° C. for 3 hours. The resulting solids were further dried in a vacuum oven at 100° C. overnight to get 4.0 g white chunks of the product polymer having a Tg of 74° C.

Examples 18 and 19. Synthesis of 100:67 and 100:300 PDD/VAc Monomer Mole Ratio Copolymers Substantially the same procedure of Example 4 was repeated except that monomer feed amounts were changed. Product isolation details were varied negligibly and solid white product chunks were obtained for each example. Data concerning these examples is presented in Table 10. Published Tg data for selected PDD/TFE copolymers is also provided in the table for comparison.

TABLE 10

|  | Composition | Feed Mole Ratio | Tg (° C.) |
|---|---|---|---|
| Ex. 4 | PDD/VAc | 100/100 | 87 |
| Ex. 17 | PDD/VAc | 100/200 | 74 |
| Ex. 18 | PDD/VAc | 100/67 | 93 |
| Ex. 19 | PDD/VAc | 100/300 | 65 |
|  | PDD/TFE | 65/35* | 160 |
|  | PDD/TFE | 87/13* | 240 |

*Mole ratio of PDD/TFE in product

Examples 20-23. Membrane Made Using PDD/VAc Copolymer

Teflon AF 2400 was dissolved in Fluorinert™ FC-770 Electronic Liquid to make 0.1% and 0.3% solutions. Two gutter layer-coated membranes GLA and GLB were created by separately depositing the Teflon AF 2400 polymer solution on polyacrylonitrile ultrafiltration SEPRO PAN 350 porous. A side of the substrate was contacted with the coating solution for 5 sec. The coated substrate was allowed to drain for 30 sec, dried in air at lower than 30% relative humidity for 5 min, and then heated in an oven at 65 to 70° C. for 30 min. An HDL (gutter layer) of Teflon AF 2400 was thus produced on each membrane. Permeance in gas permeation units (GPU) of pure gas nitrogen and oxygen through each of the gutter-coated membranes was measured. The $O_2/N_2$ selectivity of the gutter-coated membranes were calculated as the ratio of the pure gas permeances. This data is presented in Table 2.

TABLE 11

|  | GLA (0.1% solution) | GLB (0.3% solution) |
|---|---|---|
| $N_2$ Permeance (GPU) | 9770 | 2890 |
| $O_2$ Permeance (GPU) | 17260 | 5232 |
| $O_2/N_2$ Selectivity | 1.77 | 1.81 |

For Examples 20 and 22, polymers of Exs. 4 and 18, respectively were dissolved to 0.07% concentration in a solvent of a 1/1/1 by weight mixture of Novec™ HFE-7200 Engineered Fluid (3M Company, Minneapolis, Minn.)/acetone/ethanol. For Examples 21 and 23, polymers of Ex. 17 and 19, respectively, were dissolved to 0.07% concentration in a solvent of a 1/1 weight mixture of acetone/ethanol.

The solutions were each coated onto the HDL layer of different HDL/substrate samples of gutter layer membranes. The pure gas permeance through each membrane was measured for each of nitrogen, oxygen, helium and carbon dioxide. The selectivities of $O_2$, He and $CO_2$ relative to $N_2$ were calculated from the ratios of the corresponding pure gas permeance values. Results are presented in Table 12.

TABLE 12

|  | Ex. 22 | Ex. 20 | Ex. 21 | Ex. 23 |
|---|---|---|---|---|
| PDD/VAc molar feed ratio | 100/67 | 100/100 | 100/200 | 100/300 |
| Pure Gas Permeance |  |  |  |  |
| $N_2$ (GPU) | 1110 | 655 | 290 | 95 |
| $O_2$ (GPU) | 3595 | 2311 | 1164 | 450 |
| He (GPU) | 19144 | 15353 | 10352 | 5,720 |
| $CO_2$ (GPU) | 11770 | 7351 | 4420 | 1,907 |
| Selectivity |  |  |  |  |
| $O_2/N_2$ | 3.2 | 3.5 | 4.0 | 4.7 |
| $He/N_2$ | 17.4 | 23.4 | 35.7 | 60.1 |
| $CO_2/N_2$ | 10.7 | 11.2 | 15.2 | 20.0 |

Data of Table 11 shows that the GLA and GLB membranes with and HDL have active layers of conventional perfluorinated copolymers that provide very high $O_2$ and $N_2$ permeance values with $O_2/N_2$ selectivities less than 2. Thus the gutter layer did not restrict flow and selectivity was sufficiently low to not substantially adversely constrain the performance of the active layer in the composite membrane of these examples. Exs. 20-22 membranes provide lower permeance values as might be expected in view that flow through each membrane is caused by limiting resistance from the novel membrane active layer composition (i.e. PDD/VAc). However, the $O_2/N_2$ selectivities all increased to at least 3.2. The permeance decreases and selectivity increases directly with proportion of VAc monomer in the novel membrane composition. Excellent performance improvement is obtained with only a fraction of VAc monomer in the feed. For example, Ex. 22 indicates that $O_2$ permeance decreased by 32% yet the $O_2/N_2$ selectivity increased by 77% relative to GLB gutter layer membrane.

The preceding membrane fabrication examples also make apparent a surprising and extremely advantageous aspect. The highly fluorinated polymer was capable of being dissolved in solvents that were not exclusively fluorine-containing specialty fluids. In Exs. 21 and 23 the active layer copolymers incorporated relatively large fractions of VAc repeating units as implied by the comparatively low PDD/VAc reactant mole ratios. Likely due to the presence of a substantial non-halogenated component, the copolymers were soluble in completely organic, polar solvent system of acetone and ethanol. Exs. 20 and 22 active layer copolymers incorporated smaller fractions of VAc repeating units as evident from the higher PDD/VAc reactant mole ratios. Solubility of the membrane polymer was aided by including some specialty, highly fluorinated solvent in addition to acetone and ethanol.

These examples thus demonstrate that copolymer membranes according to this invention can be fabricated with organic, polar solvents. Some specialty, fluorinated solvents may be used to dissolve the copolymer. The fraction of specialty solvent depends proportionately upon the fraction of vinyl ester monomer relative to the fraction of perfluorinated monomer in the copolymer. Copolymer with more than a minimum vinyl ester fraction can be dissolved in a completely organic, polar solvent having no specialty, fluorinated solvent component of solution. Copolymer with less vinyl ester monomer content, can use solvent containing at least some specialty fluorinated solvent. Fluorinated solvents identified above are generally extremely expensive. Consequently, it is a very advantageous feature of this invention that the membranes can be fabricated with plentiful, inexpensive, readily available organic polar solvents as set forth above.

Example 24. Synthesis of a 100/160 PDD-VPI Monomer Mole Ratio Copolymer

A round bottom glass pressure vessel equipped with a magnetic stirrer is immersed into an ice bath, flushed with argon and then loaded with 10 mL of Vertrel XF, 2.56 g vinyl pivalate, 3.0 g PDD and 0.3 mL HFPO dimer peroxide (0.12 M). The vessel is sealed and the reaction mixture is warmed to room temperature by immersing into a water bath. The reaction mixture is stirred overnight at room temperature. The vessel is opened to air and 30 mL methanol is poured in with stirring. The liquid was decanted and the resulting gel-like, soft solid polymeric product was dried in an oven at 100° C. for 2 hours. The product polymer was further dried in a vacuum oven at 110° C. for 2 hours to get 5.0 g white chunks. Glass transition temperature of the product polymer was determined as 100° C.

Example 25. Synthesis of a 100/400 PDD-VPI Monomer Molar Ratio Copolymer

The procedure of Ex. 24 was repeated except that materials were 15 mL of Vertrel XF, 5.12 g vinyl pivalate, 2.44 g PDD and 0.4 mL HFPO dimer peroxide (0.12 M). Also, after methanol addition, a solution resulted that was dried at room temperature for 1 hour and then at 100° C. for an additional hour. This produced solids that were further dried in a vacuum oven at 110° C. for 2 hours to get 4.8 g white chunks of product polymer.

Examples 26 and 27 Membrane Made Using PDD/VPI Copolymer

A support membrane coated with an HDL of GLA was fabricated as described above. For Example 26, the copolymer from example 24 was dissolved in acetone/ethanol (1/1 by weight) mixture to a 0.36% solution. For Example 27, the copolymer from Example 25 was dissolved in acetone/ethanol (1/1 by weight) mixture as a 0.30% solution. The Ex. 26 and 27 solutions were coated onto the HDL of different pieces cut from the support membrane to form composite membranes. The coating procedures were the same as described in earlier examples. Pure $O_2$ and $N_2$ gases were separately permeated through the composite membranes to determine permeance values from which $O_2/N_2$ selectivities were calculated. Data for these examples is presented in Table 13.

Example 28. Membrane with a Perfluorinated Monomer/Vinyl Ester Monomer Terpolymer A stainless steel pressure vessel equipped with a magnetic stirrer was immersed in an ice bath, flushed with argon and then loaded with 10 mL of Vertrel XF, 1.72 g vinyl acetate, 2.44 g PDD and 0.5 mL HFPO dimer peroxide (0.12 M). Chlorotrifluoroethylene (1.17 g) was charged into the vessel that was then sealed. The reaction mixture was stirred and warmed to room temperature by immersing the vessel in a water bath. The reaction mixture was stirred overnight at room temperature. The vessel was opened to air and 60 mL methanol was poured in with stirring. The resulting tacky solids were washed with 20 mL methanol and dried in an oven at 100° C. for 2 hours. The solids were further dried in a vacuum oven at 100° C. for 3 hours to get 3.5 g white chunks of polymer.

The PDD/VAc/CTFE terpolymer was dissolved in a 1/1 weight ratio acetone/ethanol solution to 0.12%. The solution was coated onto a support membrane having an HDL of GLA to form a composite membrane as described in Examples 26 and 27. The membrane was subjected to pure gas permeation trials with oxygen, nitrogen, helium and carbon dioxide. The pure gas permeance values were determined and selectivities relative to nitrogen calculated therefrom. Data for this example is presented in Table 13.

The novel membranes utilizing a non-porous active selectively permeable layer comprising perfluorinated monomer and vinyl ester monomer copolymer is remarkably effective for separating gas mixtures. They are especially useful for separating oxygen from mixtures with nitrogen. The extraordinary separation performance is shown in FIG. 1 of a plot of oxygen/nitrogen selectivity a vs. oxygen permeance P in gas permeation units (GPU). The modified Robeson Permeation Limit (RPL) line shows the theoretical selective permeation upper limit predicted by Robeson in 2008. The RPL line is well known and recognized in the membrane separation industry as representing the universally applicable, theoretical maximum selectivity that can be obtained for a selectively permeable membrane at any particular permeance value. The RPL line shows that as permability increases selectivity decreases. This means that the faster the flow of migrating component through a selectively permeable membrane, the less selective the membrane performs. As can be seen from FIG. 1, the membranes of Exs. 22, 26, and 27, perform in the range of most membranes below the RPL but close to maximum theoretical performance limit. Ex. 20 membrane performance was exactly at RPL. Surprisingly, membranes of Exs. 21, 23 and 28 demonstrated performance that exceeded the state of the art maximum theoretical performance limit.

TABLE 13

|  | Ex. 26 | Ex. 27 | Ex. 28 |
|---|---|---|---|
| Molar Feed Composition |  |  |  |
| VPI (moles/100 moles PDD) | 1.60 | 4.00 |  |
| VAc (moles/100 moles PDD) |  |  | 2.00 |
| CTFE (moles/100 moles PDD) |  |  | 1.00 |
| PDD/VPI molar feed ratio | 100/160 | 100/400 |  |
| Copolymer Tg (° C.) | 100 | 91 | 68 |

TABLE 13-continued

|  | Ex. 26 | Ex. 27 | Ex. 28 |
|---|---|---|---|
| Pure Gas Permeance |  |  |  |
| $N_2$ (GPU) | 451 | 437 | 102 |
| $O_2$ (GPU) | 1454 | 1533 | 478 |
| He (GPU) |  |  | 6,188 |
| $CO_2$ (GPU) |  |  | 1,942 |
| Selectivity |  |  |  |
| $O_2/N_2$ | 3.22 | 3.51 | 4.7 |
| $He/N_2$ |  |  | 60.6 |
| $O_2/N_2$ |  |  | 19.0 |

Example 29. High Diffusion Rate Layer Permeability Measurements

Solutions were prepared from Teflon® AF 2400 in Fluorinert®770 at various concentrations (Table 14) and coated on a PAN350 membrane as described in Ex. 3. It is believed lower polymer concentration results in formation of thinner membranes. These supported membranes were tested for nitrogen permeance at feed pressures of 10, 20 and 30 psig (68.9, 137.8 and 207.7 kPa) and at ambient (atmospheric) pressure on the product side. The results shown in Table 14 for each solution are averages of the three feed pressures.

TABLE 14

| Teflon ® AF 2400 (wt %) | $N_2$ Permeance (GPU) |
|---|---|
| 0.3 | 2578 |
| 0.1 | 6184 |
| 0.05 | 12445 |

The invention claimed is:

1. A membrane separation method comprising the steps of
    (i) providing a fluid mixture of feed components,
    (ii) providing a selectively permeable separation membrane comprising a non-porous, active layer comprising an amorphous fluorinated copolymer consisting of:
        (a) a perfluorinated cyclic or cyclizable olefin monomer and
        (b) an alkoxylated monomer,
    (iii) contacting a feed-retentate side of the membrane with the mixture,
    (iv) selectively permeating the mixture through the membrane to form a permeate composition on the permeate side of the membrane opposite the feed-retentate side, and a retentate composition on the feed-retentate side of the membrane, and
    (v) recovering from the membrane at least one of (a) the permeate composition enriched in faster permeating feed components relative to the mixture, and (b) the retentate composition depleted of faster permeating feed components relative to the mixture, and in which the alkoxylated monomer is selected from the group consisting of an alkyl vinyl ester monomer having the formula $H_2C\!\!=\!\!CHOC(O)R$ in which R is a linear or branched alkyl group with 1 to 5 carbon atoms, a vinyl alcohol monomer, and a mixture of them.

2. The method of claim 1 in which the perfluorinated cyclic or cyclizable olefin monomer is perfluoro-2,2-dimethyl-1,3-dioxole.

3. A membrane separation method comprising the steps of:

(i) providing a fluid mixture of feed components,
(ii) providing a selectively permeable separation membrane comprising a non-porous active layer comprising an amorphous fluorinated copolymer consisting of:
(a) a perfluorinated cyclic or cyclizable olefin monomer;
(b) an alkoxylated monomer; and
(c) a third fluorine substituted monomer selected from the group consisting of perfluoromethyl vinyl ether (PFMVE), tetrafluoroethylene (TFE), vinyl fluoride (VF) and $CF_2$=$CFOR_f$—X wherein $R_f$ is a straight chain or branched fluoroalkyl group having 2 to 10 carbon atoms, and in which X is a group selected from $SO_2F$, $SO_3H$, $CO_2CH_3$, $CH_2OH$ and CN;
(iii) contacting a feed retentate side of the membrane with the mixture,
(iv) selectively permeating the mixture through the membrane to form a permeate composition on the permeate side of the membrane opposite the feed-retentate side, and a retentate composition on the feed-retentate side of the membrane, and
(v) recovering from the membrane at least one of (a) the permeate composition enriched in faster permeating feed components relative to the mixture, and (b) the retentate composition depleted of faster permeating feed components relative to the mixture, and in which the alkoxylated monomer is selected from the group consisting of an alkyl vinyl ester monomer having the formula $H_2C$=CHOC(O)R in which R is a linear or branched alkyl group with 1 to 5 carbon atoms, a vinyl alcohol monomer, and a mixture of them.

4. The method of claim 3 in which $R_f$ is substituted with at least one ether oxygen atom.

5. The method of claim 1 in which the alkoxylated monomer is selected from the group consisting of $H_2C$=$CHOC(O)CH_2$ (vinyl acetate), $CH_2$=$CHOC(O)C(CH_3)_3$ (vinyl pivalate), a vinyl alcohol monomer, and a mixture thereof.

6. The method of claim 1 in which the fluid mixture of feed components comprises at least two gaseous components selected from the group consisting of oxygen, nitrogen, carbon dioxide, hydrogen, helium, methane and water vapor.

7. The method of claim 1 in which the membrane further comprises a non-selectively permeable support layer coextensive with the active layer and a high diffusion rate layer (HDL) intermediate between and coextensive with the active layer and the support layer in which the high diffusion layer comprises a polymer having a permeance to nitrogen of at least 250 gas permeation units.

8. The method of claim 7 in which the membrane further comprises a second HDL positioned coextensively adjacent to the active layer on a side of the membrane opposite the support layer.

9. The method of claim 7 in which the HDL comprises a copolymer of perfluoro-2,2-dimethyl-1,3-dioxole and tetrafluoroethylene.

10. The method of claim 1 in which the step of providing the selectively permeable membrane comprises:
(ii)(a) copolymerizing a perfluorinated cyclic or cyclizable olefin monomer and an alkyl vinyl ester monomer of $H_2C$=CHOC(O)R in which R is a linear or branched alkyl group having from 1 to 5 carbon atoms, thereby forming an olefin/ester copolymer having ester functional groups, and
(ii)(b) hydrolyzing at least about 50% of the ester functional groups of the olefin/ester copolymer to alcohol.

11. A selectively permeable separation membrane comprising a non-porous active layer consisting of:
an amorphous fluorinated copolymer of a perfluorinated cyclic or cyclizable olefin monomer, and
an alkoxylated monomer selected from the group consisting of an alkyl vinyl ester monomer having the formula $H_2C$=CHOC(O)R in which R is a linear or branched alkyl group with 1 to 5 carbon atoms, a vinyl alcohol monomer, and a mixture of them.

12. The membrane of claim 11 in which the perfluorinated cyclic or cyclizable olefin monomer is perfluoro-2,2-dimethyl-1,3-dioxole.

13. A selectively permeable separation membrane comprising an active layer consisting of:
an amorphous fluorinated copolymer of a perfluorinated cyclic or cyclizable olefin monomer and
an alkoxylated monomer selected from the group consisting of an alkyl vinyl ester monomer having the formula $H_2C$=CHOC(O)R in which R is a linear or branched alkyl group with 1 to 5 carbon atoms, a vinyl alcohol monomer, and a mixture of them; and
a fluorine substituted monomer selected from the group consisting of perfluoromethyl vinyl ether (PFMVE), tetrafluoroethylene (TFE), vinyl fluoride (VF), and CF2=CFORf-X wherein Rf is a straight chain or branched fluoroalkyl group having 2 to 10 carbon atoms, and in which X is a group selected from SO2F, SO3H, CO2CH3, CH2OH and CN.

14. The membrane of claim 11 in which the alkoxylated monomer is selected from the group consisting of $H_2C$=$CHOC(O)CH_3$ (vinyl acetate), $CH_2$=$CHOC(O)C(CH_3)_3$ (vinyl pivalate), a vinyl alcohol monomer, and a mixture thereof.

15. The membrane of claim 11 which further comprises a non-selectively permeable support layer and a first high diffusion rate layer ("HDL-1" layer), the HDL-1 layer comprising a polymer having a permeance to nitrogen of at least 250 gas permeation units, and in which the support layer and the HDL-1 layer being coextensive with the active layer.

16. The membrane of claim 15 in which the HDL-1 layer is positioned intermediate between the support layer and the active layer with one side of the HDL-1 layer being in direct contact with a side of the support layer and a second side of the HDL-1 layer being in direct contact with a side of the active layer.

17. The membrane of claim 15 in which the HDL-1 layer is positioned on a side of the membrane opposite the support layer and in direct contact with a side of the active layer.

18. The membrane of claim 15 which further comprises a second high diffusion rate layer ("HDL-2" layer) comprising a polymer having a permeance to nitrogen of at least 250 gas permeation units, the HDL-2 layer being coextensive and in direct contact with a side of the active layer opposite the HDL-1 layer.

* * * * *